(12) United States Patent
Yasuda et al.

(10) Patent No.: US 7,309,362 B2
(45) Date of Patent: Dec. 18, 2007

(54) ARTIFICIAL KNEE JOINT

(75) Inventors: Kazunori Yasuda, Sapporo (JP); Wataru Yamanashi, Kyoto (JP); Shigeru Satake, Kyoto (JP)

(73) Assignee: Kyocera Corporation, Kyoto (JP)

( * ) Notice: Subject to any disclaimer, the term of this patent is extended or adjusted under 35 U.S.C. 154(b) by 453 days.

(21) Appl. No.: 10/787,062

(22) Filed: Feb. 25, 2004

(65) Prior Publication Data

US 2004/0186582 A1    Sep. 23, 2004

(30) Foreign Application Priority Data

Feb. 25, 2003    (JP)    ............... P 2003-047009

(51) Int. Cl.
    *A61F 2/38*    (2006.01)
(52) U.S. Cl. ................................... 623/20.31
(58) Field of Classification Search ... 623/20.14–20.34
    See application file for complete search history.

(56) References Cited

U.S. PATENT DOCUMENTS

| | | | |
|---|---|---|---|
| RE29,757 E * | 9/1978 | Helfet ................ | 623/20.31 |
| 4,888,021 A | 12/1989 | Forte et al. | |
| 5,219,362 A * | 6/1993 | Tuke et al. ........... | 623/20.31 |
| 5,282,870 A * | 2/1994 | Moser et al. .......... | 623/20.31 |
| 5,935,173 A * | 8/1999 | Roger et al. .......... | 623/20.31 |
| 5,997,577 A * | 12/1999 | Herrington et al. ..... | 623/20.15 |
| 6,013,103 A | 1/2000 | Kaufman et al. | |
| 6,056,779 A * | 5/2000 | Noyer et al. .......... | 623/20.32 |
| 6,406,497 B2 * | 6/2002 | Takei ................. | 623/20.31 |
| 2003/0100953 A1 * | 5/2003 | Rosa et al. ............ | 623/20.3 |
| 2004/0243244 A1 * | 12/2004 | Otto et al. ............ | 623/20.27 |

FOREIGN PATENT DOCUMENTS

| | | |
|---|---|---|
| JP | 3502291 T | 5/1991 |
| WO | 8906947 A1 | 8/1989 |

OTHER PUBLICATIONS

Japanese language office action and its English translation for corresponding Japanese application number 2003-047009 lists the references above.

* cited by examiner

*Primary Examiner*—Bruce Snow
*Assistant Examiner*—Cheryl Miller
(74) *Attorney, Agent, or Firm*—Hogan & Hartson LLP

(57) ABSTRACT

An artificial knee joint, which makes a drag (a contact stress) acting on a sliding surface upon bending small so as to evade an extraordinary abrasion and damage of a sliding surface of a tibia component and which prevents an bending angle from being decreased by preventing lifting of a femoral component in a rotational movement. The artificial knee joint comprises a femoral component to be secured to a distal portion of a femur and a tibia component to be secured to a proximal portion of a tibia, comprising an inner sliding surface and an outer sliding surface receiving a load of the femoral component at the tibia component.

In the inner sliding surface, both of a front side and a rear side are formed in a sectional shape of circular arc in the front-to-back direction thereof, while in the outer sliding surface, a front side is formed in a sectional shape of a circular arc and a rear side is formed in a linear sectional shape in the front-to-back direction thereof.

4 Claims, 7 Drawing Sheets

LATERAL CONDYLE

MEDIAL CONDYLE

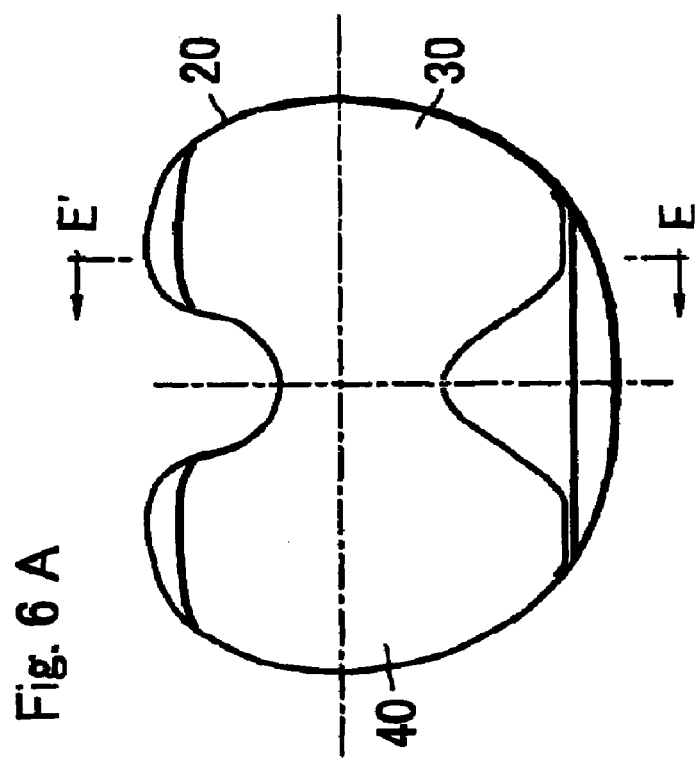
Fig. 6A
Fig. 6B
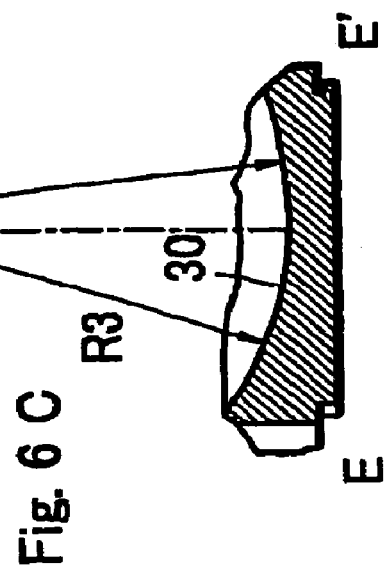
Fig. 6C

ARTIFICIAL KNEE JOINT

BACKGROUND OF THE INVENTION

1. Field of the Invention

The present invention relates to an artificial knee joint used to properly restore knee joints significantly deformed by chronic rheumatism, osteo-arthritis, pseudogout, and sudden osteonecrosis or the like.

2. Description of the Related Art

In a conventional artificial knee joint shown in FIG. 6, an inner sliding surface 30 and an outer sliding surface 40 of a tibia component 20 are shaped completely symmetrically, the inner sliding surface 30 and the outer sliding surface 40 make a circular arc having a curvature radius R3 at a front side at a longitudinal section and make a circular arc having a curvature radius R4 at a rear side at the longitudinal section, further, R3<R4 here.

In addition, in other conventional artificial knee joint shown in FIG. 7, an inner sliding surface 31 and an outer sliding surface 41 are formed, which are asymmetrical to a tibia component 21 (see U.S. Pat. No. 6,013,103).

In this artificial knee joint, the inner sliding surface 31 of the tibia component 21 is provided as a concave spherical surface of R9 and a front side of the other outer sliding surface 41 makes a circular arc having a curvature radius R7 and a rear side thereof makes a circular arc having a curvature radius R8, and further, R7<R8 here.

However, the above described conventional artificial knee joint shown in FIG. 6 involves a problem such that a large drag (a contact stress) is generated on a sliding surface by a rotational movement generated between the tibia component and a femoral component upon bending so as to bring about an extraordinary abrasion and a damage of the sliding surface of the tibia component although an R curved surface provided at the front and rear sides of the sliding surface of the tibia component allows a stability in a front-to-back direction of the femoral component upon extending the knee joint.

Further, according to a rotational operation of the femur, the femoral component is lifted along the R curved surface of the tibia component so as to bring about an excess tension to a surrounding ligaments and soft tissue, whereby a bending angle may be sometimes decreased.

In addition, in the conventional artificial knee joint shown in FIG. 7, since an inner condyle of the femoral component is completely held, if a rotational axis of the artificial knee joint is not identical with the rotational axis that is ideal for a living body due to unbalance of a ligament balance of the living body and an inefficient handling of an artificial knee joint replacement operation, a drag (a contact stress) acting on the sliding surface upon bending is made very large, and this causes the extraordinary abrasion and the damage of the sliding surface of the tibia component and further, it is feared that the excess tension is generated around the artificial knee joint and the bending angle is decreased by lifting of the femoral component in a rotational movement.

SUMMARY OF THE INVENTION

The present invention has been made taking the foregoing problems into consideration and has an object of providing an artificial knee joint, which makes it small for a drag (a contact stress) acting on a sliding surface upon bending so as to evade an extraordinary abrasion and a damage of a sliding surface of a tibia component and which prevents an bending angle from being decreased by preventing a femoral component from lifting in a rotational movement.

Therefore, in order to solve the above-described problems, according to a first aspect of the present invention, there is provided an artificial knee joint which comprises a femoral component to be secured to a distal portion of a femur and a tibia component to be secured to a proximal portion of a tibia, comprising an inner sliding surface and an outer sliding surface receiving a load of the femoral component at the tibia component, wherein the inner sliding surface is formed in a sectional shape of circular arc at the front and rear sides in the front-to-back direction thereof, while the outer sliding surface is formed in a sectional shape of circular arc at the front side in the front-to-back direction and in a linear sectional shape at the rear side thereof.

According to a preferred embodiment of the present invention, there is provided an artificial knee joint which comprises a middle portion of the inner sliding surface of the tibia component is formed in a linear shape in the front-to-back direction thereof.

According to another preferred embodiment of the present invention, there is provided an artificial knee joint which comprises the outer sliding surface of the tibia component formed in a sectional shape of circular arc in a direction orthogonal to the front-to-back direction thereof, and a curvature radius of the circular arc is gradually increased from the front side to the rear side in the front-to-back direction thereof.

According to the present invention, it is possible to naturally perform a femur external rotational operation around an inner condyle operating in a living body, further, since the inner condyle of the femur component is not held completely, it is possible to make it small for a drag (a contact stress) acting on the sliding surface upon bending so as to evade the extraordinary abrasion and the damage of the sliding surface of the tibia component, and in addition, by preventing the femur component from lifting in the rotational movement, a large bending angle can be acquired without generating the excess tension in the ligaments around the artificial knee joint.

In addition, since the sliding surface at the outer and rear side of the tibia component is formed in a linear shape in the front-to-back direction, and the femoral component is allowed to be roll-backed to the rear side of the inner condyle, even in a rotational movement supported by an outer condyle, it is possible to make it small for a drag (contact stress) acting on the sliding surface upon bending so as to evade the extraordinary abrasion and the damage of the tibia component, and in addition, by preventing the femur component from lifting in the rotational movement, a large bending angle can be acquired without generating the excess tension in the ligaments around the artificial knee joint.

In addition, according to the preferred embodiment, when the excess tension is brought about at an accessory ligament at the outside of an excessive valgus deformed knee, by allowing some external condyle supporting movement, the tension of the ligament can be absorbed and the bending angle can be increased.

In the next place, according to another preferred embodiment, since a degree of freedom in the movement in a lateral direction at the inner rear side of the tibia component is made higher, an operation for making the drag (the contact stress) acting on the sliding surface upon bending small can be strengthened.

BRIEF DESCRIPTION OF THE DRAWINGS

The above and other objectives and features of the present invention will become more apparent from the following description of a preferred embodiment thereof with reference to the accompanying drawings, throughout which like parts are designated by like reference numerals, and wherein:

FIG. 6A and FIG. 6B are a top view and a front view of a sliding member of a tibia component configuring a conventional artificial knee joint, respectively, and FIG. 6C is a cross sectional view cut along an E-E' line shown in FIG. 6A.

The present invention become more fully understood from the detailed description given hereinafter and accompanying drawings which are given by way of illustration only, and thus are not limitative of the present invention.

DESCRIPTION OF THE PREFERRED EMBODIMENTS

Figure 1:
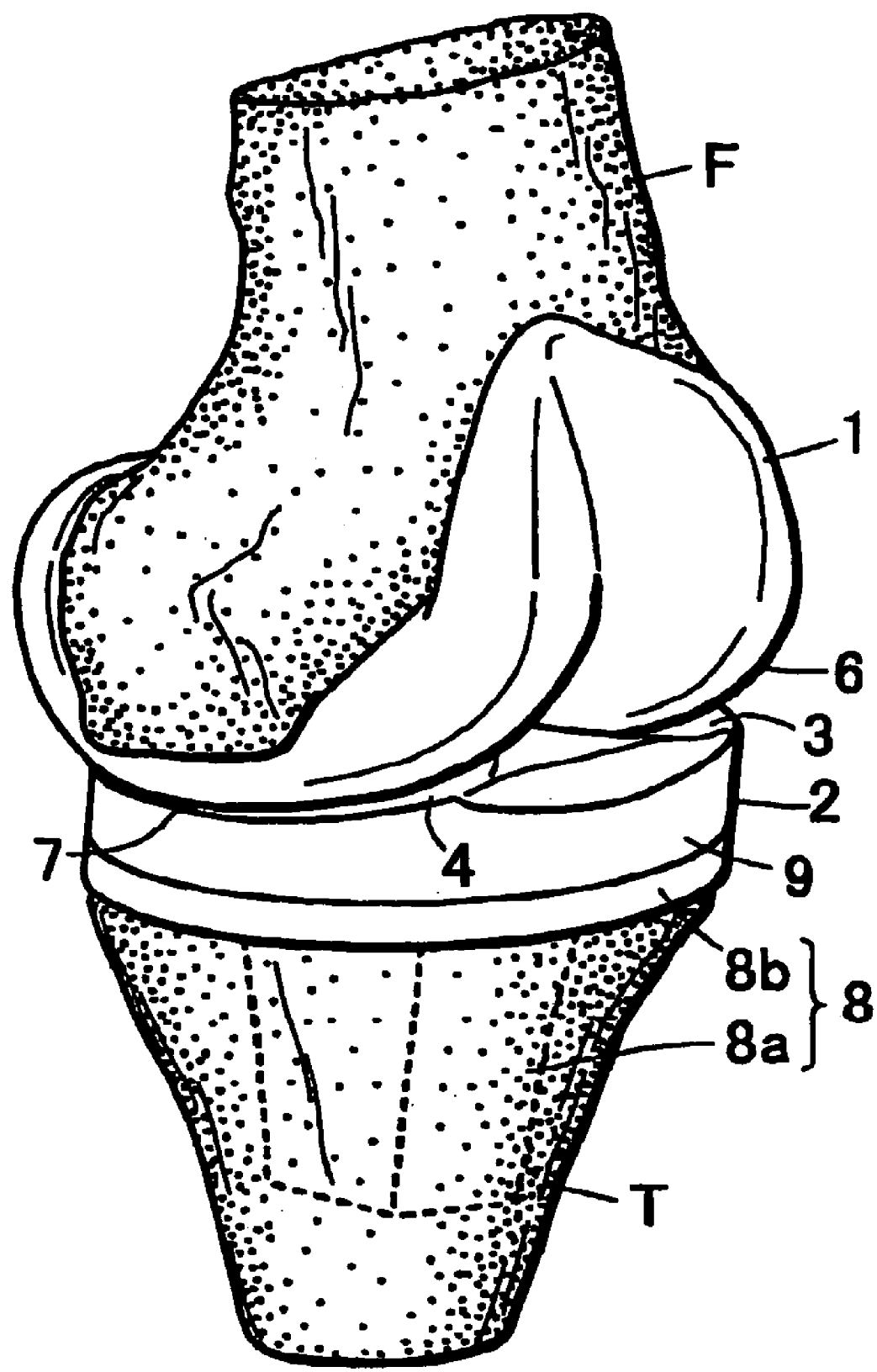
FIG. 1 is a perspective view showing a condition that an artificial knee joint according to the present invention is set on a knee joint region.

FIG. 1 shows the condition that the artificial knee joint according to the present invention is set at the knee joint region. The artificial knee joint is composed of a femoral component 1 to be secured to a distal portion of a femur F, and a tibia component 2 to be secured to a proximal portion of a tibia T. Among them, the tibia component 2 is composed of a tray member 8 in which a stem 8a to be embedded in the tibia and a tray 8b are integrally formed, and a sliding member 9 in which the femur component is sliding.

Figure 2:
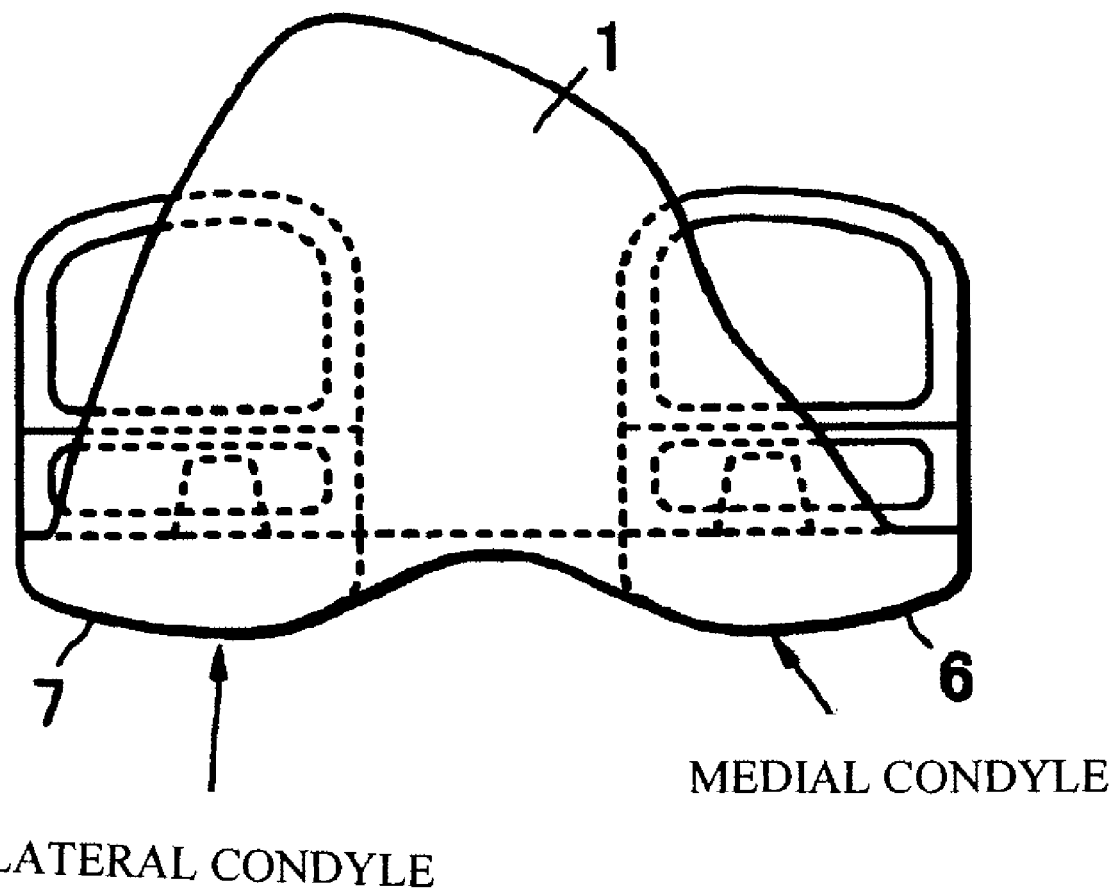
FIG. 2 is a front view of a femur component configuring the artificial knee joint shown in FIG. 1.

FIG. 2 is a front view of the femur component 1. In this femur component 1, an outer condyle sliding surface 7 and a inner condyle sliding surface G are formed at an outer condyle and an inner condyle, respectively, and they compose a joint surface by sliding an outer sliding surface 4 and an inner sliding surface 3 of the tibia component 2 to be described later.

In this case, a front-to-back (longitudinal) direction, an inner direction, and an outer direction mean an anatomic direction, namely, an anatomic direction when the components are located at the knee joint.

Figure 3D:
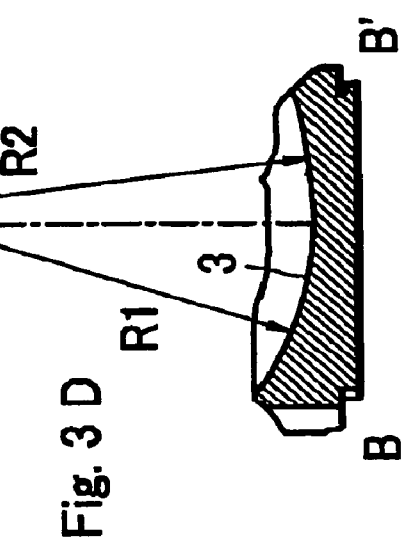
FIG. 3C and FIG. 3D are a cross sectional view cut along an A-A' line shown in FIG. 3A and a cross sectional view cut along an B-B' line shown in FIG. 3A, respectively.
Figure 3A:
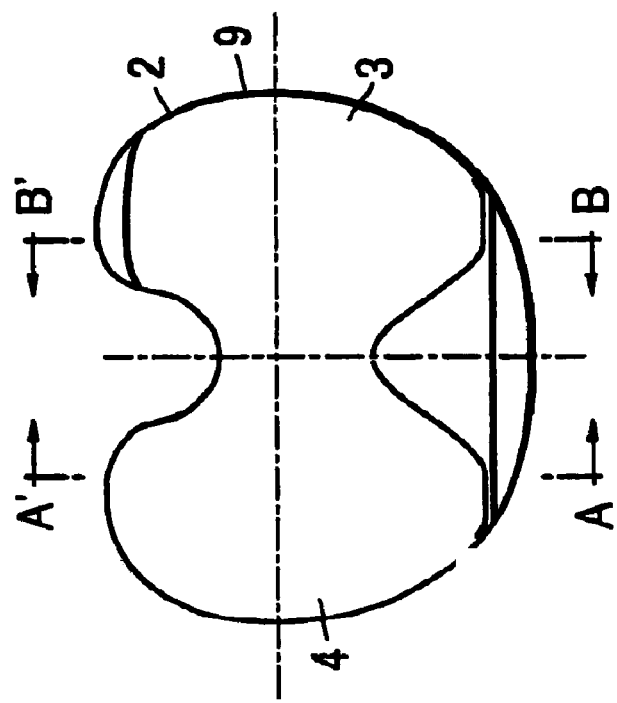
FIG. 3A and FIG. 3B are a top view and a front view of a sliding member of a tibia component configuring the artificial knee joint shown in FIG. 1, respectively.
Figure 3B:
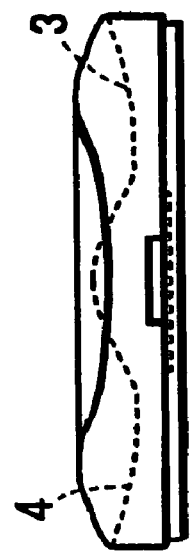
Figure 3C:
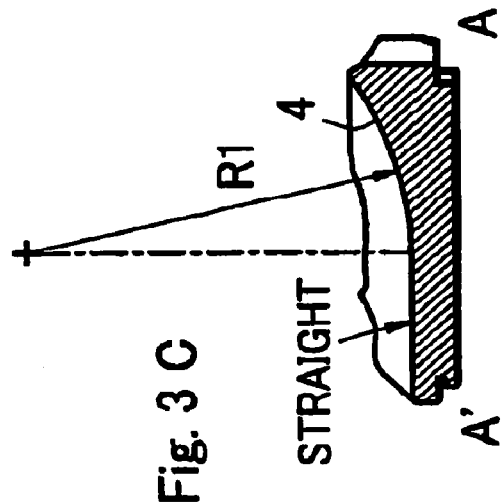

FIG. 3A and FIG. 3B are a top view and a front view of a sliding member 9 of the tibia component 2 configuring the artificial knee joint according to the present invention, and FIG. 3C and FIG. 3D are a cross sectional view cut along an A-A' line shown in FIG. 3A and a cross sectional view cut along an B-B' line shown in FIG. 3A, respectively.

Among the inner sliding surface 3 and the outer sliding surface 4 receiving a load of the femoral component 1 of the tibia component 2, in the inner sliding surface 3, the front side thereof makes a circular arc having a curvature radius R1 at a longitudinal section and the rear side thereof makes a circular arc having a curvature radius R2 (see FIG. 3D), and in the outer sliding surface 4, the front side thereof makes a circular arc having a curvature radius R1 at a longitudinal section and the rear side thereof is linearly shaped, and further, R1<R2 (see FIG. 3C).

Such femoral component 1 and such tray member 2 of the tibia component can be formed by ceramics such as alumina and zirconia, a metal such as a stainless steel, a cobalt-chromium alloy, a pure titanium and a titanium alloy or the like, and a polymer material such as a polymer polyethylene or the like. In addition, a sliding member 9 of the tibia component 2 is formed by a synthetic resin such as a high-density polyethylene or the like so as to be slidable on the femur component 1.

Figure 4B:
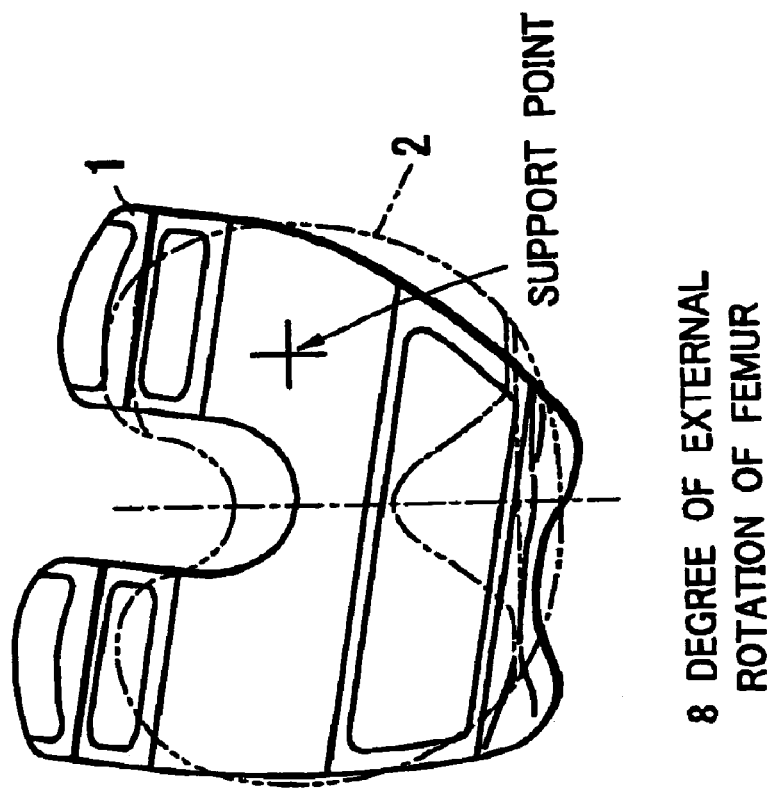
FIG. 4A and FIG. 4B are explanatory views showing a movement of the femoral component against the tibia component upon bending.
Figure 4A:
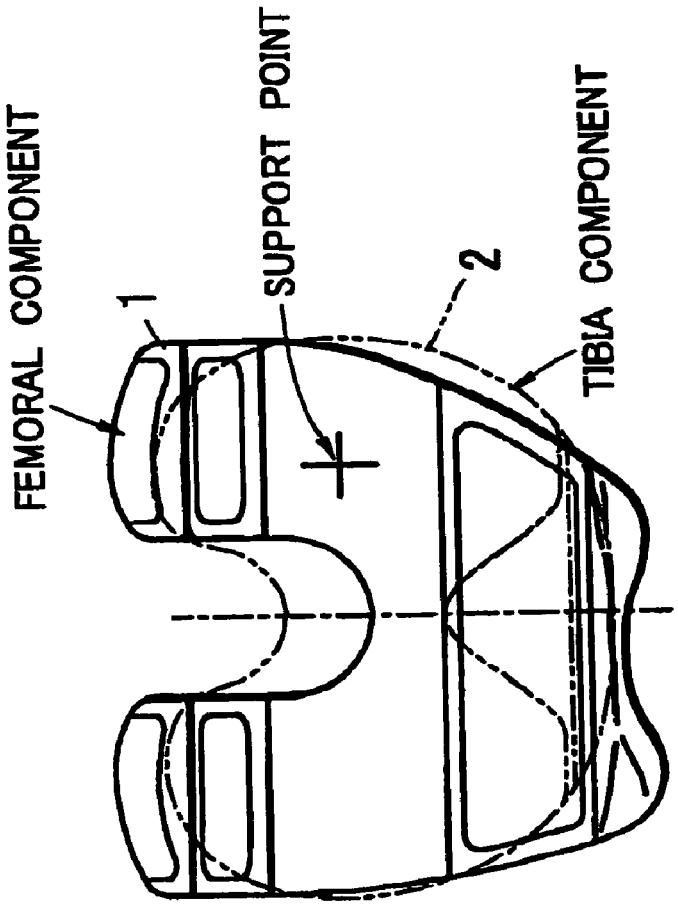

FIG. 4 is an explanatory view showing the movement of the femur component 1 against the tibia component 2. In FIG. 4, the right side indicates an inner side, and the left side indicates an outer side. As shown in FIG. 4, upon bending a knee, the external rotational movement is also generated.

In this case, as shown in FIG. 3, an R curved surface is provided at the front side and the rear side of the inner sliding surface 3 so as to tend to inhibit the sliding of the inner condyle in the femur component 2. On the other hand, since the rear side of the outer sliding surface 4 is linearly shaped in a front-to-back (longitudinal) direction, inhibition of the sliding of the outer condyle in the femur component 1 is reduced. Accordingly, as shown in FIG. 4, the femur component 1 carries out the external rotation around the inner condyle and in this time, by making it small for a resistance (abrasion) between the outer condyle sliding surface 7 of the femur component 1 and the outer sliding surface 4 of the tibia component 2, the external rotation can be smoothly made.

Accordingly, the external rotational operation around the inner condyle operating in the living body can be naturally carried out.

In addition, since the inner condyle of the femur component 1 is not held completely, by making it small for the drag (the contact stress) acting on the sliding surface upon bending, it is possible to evade the extraordinary abrasion and the damage of the sliding surface of the femur component 2.

In addition, even in a normal rotational movement (with no bending), by preventing lifting of the tibia component 2, it is possible to acquire a large bending angle without generating the excess tension at the ligament around the artificial knee joint. Further, the inner condyle of the femur component 1 is not held completely, therefore, as a result of the artificial knee joint replacement operation, even if the femur component 1 and the tibia component 2 are embedded in off-balance of the living body, it is possible to acquire a large bending angle without the excess tension in the ligament around the artificial knee joint.

Further, since the sliding surface at the outer rear side of the tibia component 2 is made in a linear shape in the front-to-back direction, and the femoral component 1 is allowed to be roll-backed to the rear side of the inner condyle, even in a rotational movement supported by the outer condyle, it is possible to make it small for the drag (the contact stress) acting on the sliding surface upon bending so as to evade the extraordinary abrasion and the damage of the tibia component 2, and in addition, by preventing the femur component 1 from lifting in the rotational movement, a large bending angle can be acquired without generating the excess tension in the ligaments around the artificial knee joint.

Figure 5:
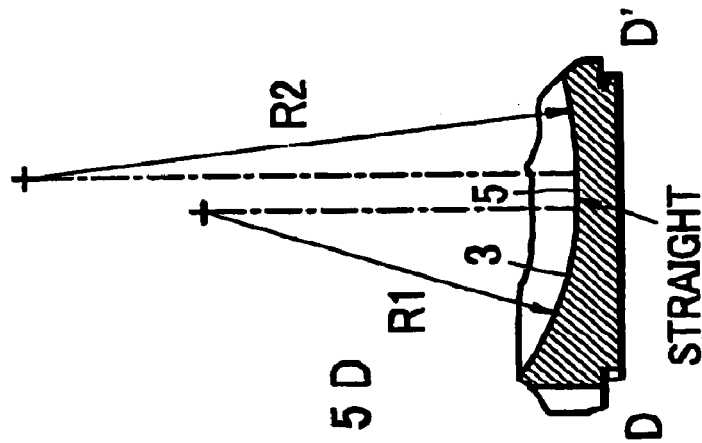
FIG. 5A and FIG. 5B are a top view and a front view or a sliding member of a tibia component showing other embodiment of the present invention, respectively.
FIG. 5C and FIG. 5D are a cross sectional view cut along an C-C' line shown in FIG. 5A and a cross sectional view cut along an D-D' line shown in FIG. 5A, respectively.
Figure 5:
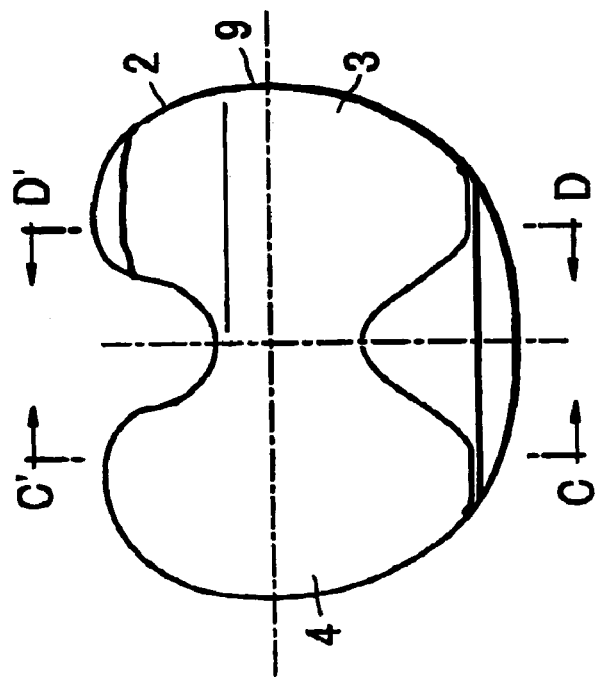
Figure 5:
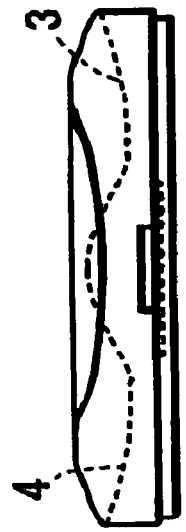
Figure 5:
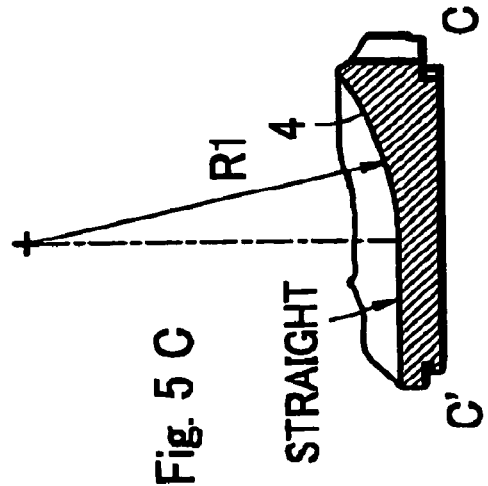
Figure 7D:
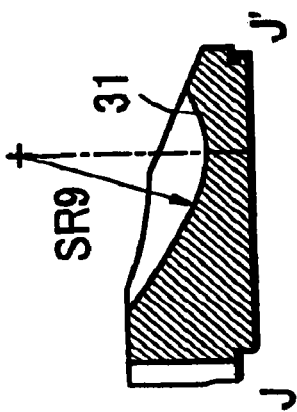
FIG. 7C and FIG. 7D are a cross sectional view cut along an H-H' line shown in FIG. 7A and a cross sectional view cut along a J-J' line shown in FIG. 7A.
Figure 7A:
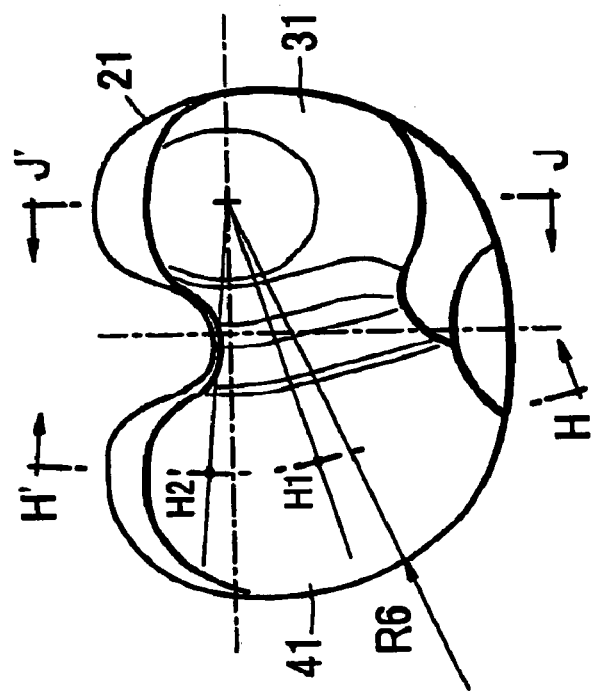
FIG. 7A and FIG. 7B are a top view and a front view of a sliding member of a tibia component configuring another conventional artificial knee joint, respectively.
Figure 7B:
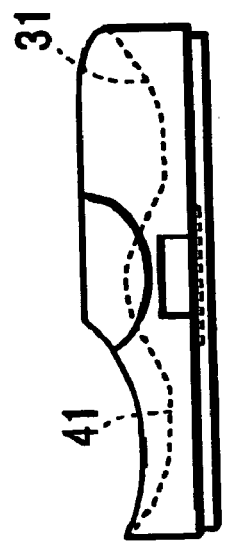
Figure 7C:
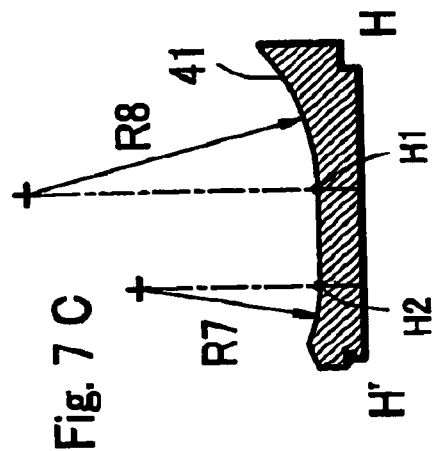

In the next place, FIG. 5 shows other embodiment. As shown in this drawing, the inner sliding surface 3 provided at a sliding member in the tibia component 2 is different from the embodiment shown in FIG. 3 in that a linear surface is provided in the front-to-back direction at a middle portion 5 between the R curved surface at the front side (the circular arc R1) and the R curved surface at the rear side (the circular arc R2).

According to such a configuration, when the excess tension is brought about at an accessory ligament at the outside of an excessive valgus deformed knee, by allowing some external condyle supporting movement, the tension of the ligament can be absorbed and the bending angle can be increased.

In addition, it is preferable that the outer sliding surface 4 of the tibia component 2 is shaped in a circular arc in a direction orthogonal to the front-to-back direction (see FIG. 2), and the curvature radius of this circular arc is gradually increased from the front side to the rear side.

Depending on such a configuration, since a degree of freedom in the movement in the lateral direction at the inner rear side of the tibia component 2 is made higher, the operation for making the drag (the contact stress) acting on the sliding surface upon bending small can be strengthened.

The embodiments of the present invention are described above, however, the present invention is not limited to the above-described embodiments, and an arbitrary embodiment can be available within a scope of the present invention.

As described above, according to the artificial knee joint of the present invention, since the artificial knee joint comprises the femoral component to be secured to the distal portion of the femur and the tibia component to be secured to the proximal portion of the tibia, provided with the inner sliding surface and the outer sliding surface receiving the load of the femoral component at the tibia component and in the inner sliding surface, the both of the front side and the rear side are formed in a sectional shape of circular arc in the front-to-back direction, and in the outer sliding surface, the front side makes a circular arc at the longitudinal section and the rear side is made in a linear shape, the femur external rotational operation around the inner condyle operating in the living body can be naturally carried out, and the inner condyle of the femur component is not held completely, and this results in making it possible to make the drag (the contact stress) acting on the sliding surface upon bending small and to evade the extraordinary abrasion and the damage of the sliding surface of the tibia component. In addition, by preventing lifting of the femur component in the rotational movement, it is possible to acquire a large bending angle without generating the excess tension in the ligament around the artificial knee joint. Further, the inner condyle of the femur component is not held completely, therefore, as a result of the artificial knee joint replacement operation, even if the femur component and the tibia component are embedded in off-balance of the living body, it is possible to acquire a large bending angle without the excess tension in the ligament around the artificial knee joint. In addition, since the sliding surface at the outer rear side of the tibia component is made in a linear shape in the front-to-back direction, and the femoral component is allowed to be roll-backed to the rear side of the inner condyle, even in a rotational movement supported by the outer condyle, it is possible to make it small for the drag (the contact stress) acting on the sliding surface upon bending so as to evade the extraordinary abrasion and the damage of the tibia component, and in addition, by preventing the femur component from lifting in the rotational movement, a large bending angle can be acquired without generating the excess tension in the ligaments around the artificial knee joint.

In addition, by making the middle portion of the inner sliding surface of the tibia component into a linear shape at the longitudinal section, when the excess tension is brought about at an accessory ligament at the outside of an excessive valgus deformed knee, by allowing some external condyle supporting movement, the tension of the ligament can be absorbed and the bending angle can be increased.

In addition, in the case that the outer sliding surface of the tibia component is shaped in a circular arc in a direction orthogonal to the longitudinal direction, and the curvature radius of this circular arc is gradually increased from the front side to the rear side, a degree of freedom in the movement in the lateral direction at the inner rear side of the tibia component is made higher, the operation for making it small for the drag (the contact stress) acting on the sliding surface upon bending can be strengthened.

What is claimed is:

1. An artificial knee joint which comprises a femoral component to be secured to a distal portion of a femur and a tibia component to be secured to a proximal portion of a tibia, comprising a medial sliding surface and a lateral sliding surface for receiving a load of the femoral component at the tibia component, wherein the medial sliding surface is formed in a sectional shape of circular arc at the anterior and posterior side(s) in the anterior-to-posterior direction thereof, while the lateral sliding sectional shape of circular arc at the anterior side and in a sectional shape of linear at the posterior side(s) in the anterior-to-posterior direction thereof, wherein the anterior side of the medial sliding surface makes a circular arc having a curvature radius $R_1$ at a longitudinal section and the posterior side makes a circular arc having a curvature radius $R_2$, wherein $R_1 < R_2$.

2. An artificial knee joint according to claim 1, wherein a middle portion of the medial sliding surface of the tibia component is formed in a linear sectional shape in the anterior-to-posterior direction.

3. An artificial knee joint according to claim 1, wherein the lateral sliding surface of the tibia component is formed in a sectional shape of circular arc in a direction orthogonal to the anterior-to-posterior direction thereof, and a curvature radius of the circular arc in said orthogonal direction is gradually increased from the anterior side to the posterior side in the longitudinal direction thereof.

4. An artificial knee joint according to claim 1, wherein the anterior side in the lateral sliding surface makes a circular arc having a curvature R1 at a longitudinal section.

* * * * *